United States Patent
Peng

(10) Patent No.: US 10,184,107 B2
(45) Date of Patent: Jan. 22, 2019

(54) ELECTRIC OVUM DENUDING DEVICE AND OVUM DENUDING METHOD

(71) Applicants: Jianjun Peng, Changsha (CN); HUNAN CHANGSHA AO FIGURE BIOLOGICAL TECHNOLOGY CO., LTD., Changsha (CN)

(72) Inventor: Jianjun Peng, Changsha (CN)

(73) Assignee: HUNAN CHANGSHA AO FIGURE BIOLOGICAL TECHNOLOGY CO., LTD., Changsha (CN)

( * ) Notice: Subject to any disclaimer, the term of this patent is extended or adjusted under 35 U.S.C. 154(b) by 118 days.

(21) Appl. No.: 15/323,719

(22) PCT Filed: Jul. 2, 2015

(86) PCT No.: PCT/CN2015/083133
§ 371 (c)(1),
(2) Date: Jan. 3, 2017

(87) PCT Pub. No.: WO2016/004830
PCT Pub. Date: Jan. 14, 2016

(65) Prior Publication Data
US 2017/0166865 A1   Jun. 15, 2017

(30) Foreign Application Priority Data

Jul. 6, 2014   (CN) .......................... 2014 1 0317452

(51) Int. Cl.
*C12N 5/075*   (2010.01)
*C12M 1/00*   (2006.01)
(Continued)

(52) U.S. Cl.
CPC .......... *C12N 5/0609* (2013.01); *A61B 17/435* (2013.01); *A61D 19/04* (2013.01);
(Continued)

(58) Field of Classification Search
CPC .. C12N 5/0609; C12N 2509/10; C12M 41/48; C12M 21/06; C12M 45/02; C12M 45/09; C12M 47/04
(Continued)

(56) References Cited

U.S. PATENT DOCUMENTS 6,838,278 B2   1/2005   Fortino
7,972,575 B2   7/2011   Lind
(Continued)

FOREIGN PATENT DOCUMENTS

CN   201150570 Y   11/2008
CN   101984923 A   3/2011
(Continued)

OTHER PUBLICATIONS

European Search Report dated Feb. 12, 2018 in the corresponding European application(application No. 15818614.8).
(Continued)

*Primary Examiner* — Navin Natnithithadha
*Assistant Examiner* — Sunita Reddy
(74) *Attorney, Agent, or Firm* — Kilpatrick Townsend & Stockton LLP

(57) ABSTRACT

An electric ooycte denuding device and an ooycte denuding method are provided. The electric oocyte denuding device includes an oocyte denuding pipette: a manipulating handle; and a drive module, a control module, a display module, a power module, a memory, a bulb, and/or a voice module, and/or a pressure sensor, and/or a control box, and/or a foot-operated switch controller, which form an integrated type or a separated type electric ooycte denuding device. A stepper motor provides the power for blowing and sucking to denude the granular cells surrounding an oocyte.

16 Claims, 12 Drawing Sheets

(51) Int. Cl.
*A61D 19/04* (2006.01)
*A61B 17/435* (2006.01)
*C12M 3/00* (2006.01)
*C12M 1/36* (2006.01)
*C12M 1/33* (2006.01)
*B01L 3/02* (2006.01)

(52) U.S. Cl.
CPC ........... *B01L 3/0227* (2013.01); *C12M 21/06* (2013.01); *C12M 41/48* (2013.01); *C12M 45/02* (2013.01); *C12M 45/09* (2013.01); *C12M 47/04* (2013.01); *B01L 3/0237* (2013.01); *B01L 2200/0684* (2013.01); *C12N 2509/10* (2013.01)

(58) Field of Classification Search
USPC ..................................................... 600/33–35
See application file for complete search history.

(56) References Cited

U.S. PATENT DOCUMENTS

| | | | |
|---|---|---|---|
| 2002/0020233 A1 | 2/2002 | Baba et al. | |
| 2002/0116732 A1* | 8/2002 | Christmann | A01K 67/0275 800/19 |
| 2004/0039247 A1 | 2/2004 | Nash | |
| 2005/0246783 A1* | 11/2005 | Christmann | A01K 67/0275 800/19 |
| 2008/0097144 A1* | 4/2008 | Cecchi | A61B 17/435 600/33 |
| 2008/0124787 A1* | 5/2008 | Christmann | A01K 67/0275 435/285.1 |
| 2009/0117008 A1* | 5/2009 | Lind | B01L 3/0227 422/400 |
| 2009/0227833 A1 | 9/2009 | Arabia et al. | |
| 2012/0116245 A1 | 5/2012 | Steiner | |
| 2012/0196358 A1 | 8/2012 | Burbank et al. | |

FOREIGN PATENT DOCUMENTS

| | | |
|---|---|---|
| CN | 202688311 U | 1/2013 |
| CN | 103110449 A | 5/2013 |
| CN | 203169276 U | 9/2013 |
| CN | 104055560 A | 9/2014 |
| EP | 1885498 A1 | 2/2008 |
| GB | 2386571 A | 9/2003 |
| WO | 2010141320 A1 | 12/2010 |
| WO | 2014100294 A1 | 6/2014 |

OTHER PUBLICATIONS

The First Office Action issued by the Chinese Patent Office dated Oct. 27, 2015 for the corresponding Chinese Patent Application No. 2014103174522.

* cited by examiner

ELECTRIC OVUM DENUDING DEVICE AND OVUM DENUDING METHOD

This application is the national phase of International Application No. PCT/CN2015/083133, titled "ELECTRIC OVUM DENUDING DEVICE AND OVUM DENUDING METHOD", filed on Jul. 2, 2015, which claims the benefit of and priority to Chinese patent application No. 201410317452.2 titled "ELECTRIC OOCYTE DENUDING DEVICE AND OOCYTE DENUDING METHOD THEREFOR", filed with the Chinese State Intellectual Property Office on Jul. 6, 2014, the entire disclosures of both applications are incorporated herein by reference.

FIELD

The present application relates to a reproduction laboratory apparatus, particularly to an electric oocyte denuding device and an oocyte denuding method therefor, and relates to the technical field of laboratory micromanipulation.

BACKGROUND

Oocyte denudation is an important part of routine work of a reproduction laboratory, and involves removing granular cells of an oocyte-corona-cumulus complex which are pre-digested by an enzyme, to assess the maturity of an oocyte and facilitate micromanipulations, such as for intracytoplasmic sperm injection (abbreviated as ICSI), granular cells are required to be removed before cryopreservation of the oocyte; for in vitro fertilization (abbreviated as IVF), such as IVF in microdrop method or IVF in test tube method, it is required to remove granular cells surrounding the oocyte, to assess fertilization condition. The oocyte denudation plays an important role in the above-mentioned manipulations, and directly affects the effect of subsequent manipulation steps.

For decades, oocyte denuding tools remain essentially unchanged, and are completely manually operated. Conventional oocyte denuding pipettes include an oocyte denuding needle and an oocyte denuding Pasteur pipette, which respectively have corresponding latex bulbs sleeved thereon, to constitute respectively a needle type oocyte denuding tool and a Pasteur pipette type oocyte denuding tool. A conventional oocyte denuding method mainly includes repeatedly pressing a latex bulb by fingers to provide a power for suctioning and blowing, to allow an oocyte-corona-cumulus complex pre-digested by hyaluronidase or an oocyte-corona-cumulus complex digested by a sperm after performing an IVF in test tube method to enter and exit from an orifice of an oocyte denuding pipette to remove granular cells, or to allow an oocyte in an oocyte-corona-cumulus complex adhered to the bottom of a culture dish after performing an IVF in microdrop method to be separated from the oocyte-corona-cumulus complex under the action of a suction force, and then to repeatedly blow and suction the oocyte to remove remaining granular cells. In another solution, an oocyte denuding pipette is connected to a mouth pipette by a hose to form a mouth pipette type oocyte denuding tool, and its mouthpiece is placed into an oral cavity, and the oocyte-corona-cumulus complex is by blew and aspirated by the oral cavity repeatedly to enter and exit from an orifice of the oocyte denuding pipette to remove granular cells. According to the tightness of bonding of granular cells of each oocyte-corona-cumulus complex, the degree of difficulty in removal of the granular cells varies, and the number of times of aspirating and blowing ranges from several times to tens of times.

A Patent titled "ORAL BALLOON TYPE OOCYTE DENUDING DEVICE" (Patent No. CN200720157432.9) discloses an oral balloon type oocyte denuding tool for removing an oocyte-corona-cumulus complex around an oocyte. It includes a micropipette and a hose sleeved on a rear end of the micropipette, and a tail end of the hose is connected with a soft balloon. In operation, the balloon is placed between upper teeth and lower teeth of an oral cavity, and is controlled by occluding teeth to provide a power for blowing and suctioning, to allow the oocyte to repeatedly and gently enter and exit from a tip of the micropipette, thereby achieving the purpose of removing most of granular cells surrounding the oocyte. In this invention, the mouthpiece of the mouth pipette is replaced by the balloon, and the effect of suctioning and blowing is achieved by squeezing the balloon through teeth occluding. Compared with the method using the mouth pipette, his method can avoid the risk of polluting the oocyte by expiration.

A Patent "OOCYTE DENUDING NEEDLE" (Patent No.: CN201220219074.0) provides an oocyte denuding needle applicable to oocytes of all sizes. This invention is a hollow oocyte denuding needle for removing granular cells surrounding the oocyte. The invention only makes changes to the structure of the oocyte denuding needle, and using the same oocyte denuding method as the conventional oocyte denuding method.

A Patent "NOVEL TEST-TUBE BABY OOCYTE DENUDING MANIPULATOR" (Patent No. CN201320050412.7) provides an oocyte denuding manipulator consisting of a handheld pressing device and an oocyte suctioning device. The handheld pressing device is composed of a pressing rod cap, a pen cap, a rear shell, a spring, a pressing rod and a front shell, and the oocyte suctioning device is composed of a gasbag, a PS tube, a needle seat and an oocyte denuding pipette. The gasbag, the PS tube, the needle seat and the oocyte denuding pipette are successively installed on a lower-middle portion of the rear shell from top to bottom; and a push button connected to a slide fastener is installed in the middle of the front shell. This invention has a significantly improved manipulation performance compared with the conventional latex bulb.

However, the oocyte denuding apparatuses in the conventional technology have the following deficiencies.

First, the control is inaccurate, and various risks exist. In the conventional oocyte denuding technology, it depends on the muscle power of an operator to control the latex bulb of an elastic operating element, the mouth pipette, the oral balloon, and the gasbag of the oocyte denuding tools. When the latex bulb, the oral balloon and the gasbag are compressed and deformed under the action of an external force, the elasticity possessed by the materials of these members has capabilities of releasing the compressive deformation and restoring to the original state, which is a power source for this kind of manual oocyte denuding tools to generate a suction force. A squeezing force applied to the above elastic operating element by the operator is a power source for this kind of manual oocyte denuding tools to generate a blowing force. For the mouth pipette type oocyte denuding tools, the function of the oral cavity is similar to the function of the elastic operating element of the above oocyte denuding tool, the difference lies in that, in the mouth pipette type oocyte denuding tools, the blowing and the suctioning are both processes in which powers are applied by an operator actively. The processes in which the suctioning force and the blowing force are generated and converted are always accompanied by a counter balance between the pressing force and the restoring force of the elastic element. In oocyte denudation, especially in an initial stage of oocyte denudation, the oocyte-corona-cumulus complex is slightly larger than an inner diameter of an orifice of the oocyte denuding pipette, and may block the orifice of the oocyte denuding pipette when passing through there, which is reflected as a reduction in the velocity of the oocyte-corona-cumulus complex passing through the orifice of the oocyte denuding pipette. After the operator adjusts to increase the suctioning force or the blowing force, especially when increasing the blowing power, once the oocyte-corona-cumulus complex passes through the orifice of the oocyte denuding pipette, the operator cannot stop timely, causing that the balance between the interconnected two processes of suctioning and blowing is lost, and the volume variations caused in the two processes are not consistent with each other, for example, the volume variation caused in the blowing process is greater than the volume variation caused in the suctioning process, resulting in that a series of bubbles are blown out. The oocyte-corona-cumulus complex or the oocyte is adhered to the peripheries of the bubbles, and are floating on the surface of liquid droplets of a culture medium along with the bubbles. The operation interface of oocyte denudation and the bubbles are presented on different focusing planes, and the oocyte-corona-cumulus complex or the oocyte adhered to the bubbles may be located at any position on the surface of the bubbles as well, hence it requires to adjust the focus length of the microscope continuously to look for the oocyte-corona-cumulus complex or the oocyte on the peripheries of the bubbles, causing the total oocyte denuding operation time to be prolonged, which not only increases the risk of damaging the oocyte due to the prolonged in vitro operation time, but also has a substantial risk of losing the oocyte. For trying to avoid generation of the bubbles as much as possible, an operator generally utilizes the oocyte denuding pipette to absorb several microliters of culture medium in advance and remains the absorbed culture medium in the tip of the oocyte denuding pipette, so as to compensate the inconsistent volume variations in the processes of blowing and suctioning, to allow the liquid column within the oocyte denuding pipette to have a height far beyond the height of the liquid in the culture dish.

The inaccurate control in the conventional oocyte denudation method exposes the oocytes or zygotes to a risk caused by temperature fluctuation. Temperature is one of the most important factors affecting the quality of the oocytes, zygotes and embryos. The basal body temperature of a human being is 37 degrees Celsius, the in vitro operation is to try to keep the temperature of the environment where the oocytes or the zygotes are located to be 37 degrees Celsius. Generally, in order to have cleaner air, the oocyte denuding operation is performed on a ventilated ultra-clean bench, the ultra-clean bench has a temperature of about 37 degrees Celsius, a room temperature is about 25 degrees Celsius, and the temperature of the culture medium in the culture dish where the oocyte-corona-cumulus complex is located is close to the temperature of the ultra-clean bench. A tip portion of the oocyte denuding pipette is very thin and small, and in the case that the oocyte is denuded manually, the liquid level of the culture medium in the tip portion of the oocyte denuding pipette is much higher than the liquid level of the culture medium in the culture dish. Only about 0.1 µL of culture medium is in a tip end, submerged in the culture medium in the culture dish, of the oocyte denuding pipette and has a temperature close to the temperature of the culture medium in the culture dish, and a rest part of the oocyte denuding pipette is exposed outside of the culture medium in the culture dish. In this way, the oocyte denuding pipette has two regions with quite different temperatures, which includes a first region, which is the tip end of the oocyte denuding pipette beneath the liquid level of the culture medium in the culture dish, and has a temperature close to that the temperature of the culture medium in the culture dish; and a second region, which is the rest part of the oocyte denuding pipette not submerged in the culture medium of the culture dish and has a temperature close to the room temperature. When the length of the liquid column of the culture medium suctioned into the oocyte denuding pipette is higher than the liquid level of the culture medium in the culture dish, heat is quickly taken away by wind through the glass pipette wall of the oocyte denuding pipette, the oocyte or zygote moves back and forth in the environments with a temperature difference above a few degrees Celsius, causing a risk of damaging the oocyte or zygote due to temperature fluctuations. A low temperature has effects on the oocytes and zygotes including decreasing the level of metabolism and altering organelle morphology and organelle function of the oocytes and zygotes. For example, at a temperature of 33 degrees Celsius, the spindle will begin to be depolymerized within 5 minutes and will completely disappear within 10 minutes. If the same ovum is heated to 37 degrees Celsius, the spindle may be completely recovered within 10 minutes. If the temperature drops to 28 degrees Celsius, the spindle is depolymerized at an increased velocity, and the time period till the spindle completely disappears is shortened, further, it requires a longer time for the spindle to recover after being heated. If the spindle is depolymerized in an environment with a temperature of 25 degrees Celsius, the spindle can hardly recover within twenty minutes after being heated to 37 degrees Celsius. In the recovering period, if cell cycle variations occur, the number of chromosomes will be abnormal. It is generally believed that the temperature of a human oocyte and a zygote during the in vitro manipulation process must be maintained in a relatively constant range, such as 35 degrees Celsius to 37 degrees Celsius, and in the manipulation process, fluctuations of temperature should be minimized as far as possible. In oocyte denudation, for trying to minimize this kind of risk, it requires that the liquid column of the culture medium suctioned into the oocyte denuding pipette should be located below the liquid droplets in the culture dish. As an example that the culture medium in the culture dish where the oocyte-corona-cumulus complex is located has a height about 2.5 mm and an included angle between the oocyte denuding pipette and the bottom of the culture dish is 30 degrees, the length of the liquid column in the oocyte denuding pipette has to be less than 5 mm to make sure that the liquid level of the culture medium in the oocyte denuding pipette is below the liquid level of the liquid droplets in the culture dish. The tip end of the oocyte denuding pipette is very thin and small, and an inner diameter of the tip of the pipette is generally 150 µm, and the volume of the culture medium having a height of 5 mm in the tip of the pipette is about 0.1 µL. In the culture medium with such a tiny volume, it is almost impossible to control the elastic operation element of the oocyte denuding tool through muscle power of the operator to drive the oocyte-corona-cumulus complex to enter and exit from the oocyte denuding pipette under conditions of not generating bubbles and adjusting the velocity appropriately.

Second, the operation has a strong subjectivity, and cannot be standardized. The oocyte denuding operation requires a gentle blow, but the "gentle blow" cannot be explicitly defined, different operators have different subjective feelings on the "gentle blow", which are reflected as significant differences in the depth and velocity of pressing the latex bulb, pressing the spring pressing rod, expirating/aspirating, and teeth occluding in using the above conventional oocyte denuding tools. These differences are directly reflected as a difference in length of liquid columns of the culture medium suctioned into the oocyte denuding pipette and a difference in velocity of the oocyte-corona-cumulus complexes passing through the orifice of the oocyte denuding pipette, and indirectly reflected as a difference in degree of risks of damaging the oocytes caused by temperature fluctuations and a difference in magnitudes of action forces on the oocyte-corona-cumulus complexes. The flow rate and the pressure of liquid are in a positive relationship, and when the diameter of the spout is certain, the faster the flow rate of the liquid, the higher the pressure at the spout. Controlling the frequency of blowing and suctioning can adjust the flow rate of the liquid, to achieve the adjustment to the pressure at the spout, and further achieve the adjustment to the suctioning force and blowing force applied on the oocyte-corona-cumulus complexes. That is, as the frequency of blowing and suctioning is increased, the suctioning force and the blowing force acted on the oocyte-corona-cumulus complexes are also increased, and further, the acting force for removing the granular cells is also correspondingly increased, and the velocity of the removal is increased. Therefore, the velocity of oocyte denudation may be adjusted by adjusting the frequency of blowing and suctioning. In the conventional oocyte denuding tools, the suctioning force and the blowing force acted on the oocyte-corona-cumulus complexes are adjusted by adjusting the depth and velocity of pressing the latex bulb, pressing the spring pressing rod, expirating/aspirating, and teeth occluding. In one complete oocyte denuding process of the oocyte-corona-cumulus complex, blowing and suctioning may be performed at multiple velocities, and correspondingly there are multiple blowing forces and suctioning forces of different magnitudes. Different blowing forces and suctioning forces and the durations thereof, especially an excessive fierce blowing force and an excessive fierce suctioning force and the durations thereof, may have different degrees of potential negative effects on the oocytes, and if the blowing and suctioning are excessively fierce, the oocyte may be ruptured and disintegrated. In manual oocyte denudation, an operator makes judgment and adjustment completely depending on subjective experiences, and cannot quantify the specific operation details, and correspondingly, cannot provide specific objective data of the whole oocyte denuding process. Whatever the embryos have a high quality or a low quality, when trying analyzing reasons in the oocyte denuding process, it cannot derive a valuable conclusion by reviewing the oocyte denuding operation process or comparing operations performed by different operators.

Third, the working load is huge. In the conventional oocyte denuding process, each time of blowing and suctioning the oocyte-corona-cumulus complex must corresponds to one time of pressing/releasing the elastic element or one action of blowing/aspirating by the oral cavity. In the conventional oocyte denuding tools either operated by a single hand or double hands, or controlled by the oral cavity, for achieving a best control effect, the operator needs to maintain the counter balance always accompanied in the conversion process of the suctioning force and the blowing force, thus, muscles of his fingers or oral cavity of the operator are always in a tensioned state, which results in physical fatigue of the operator. Further, the conventional oocyte denuding tool has risks of damaging the oocytes due to prolonged operation time and temperature fluctuations, and a heavy risk of losing the oocytes, which also places an increased psychological burden on the operator.

Therefore, to address the above technical issues, it is indeed necessary to provide an advanced electric oocyte denuding device and an oocyte denuding method thereof, to overcome the above mentioned drawbacks in the conventional technology.

SUMMARY

For addressing the above issues, an object of the present application is to provide an electric oocyte denuding device which has a high precision, a high standardization, an improved comfort and a high degree of automation.

Another object of the present application is to provide an oocyte denuding method which employs the above electric oocyte denuding device.

To achieve the first object, the technical solution employed in the present application is as follows. An electric oocyte denuding device includes an oocyte denuding pipette; a manipulating handle; and a drive module, a control module, a power module, a memory and a bulb which are mounted in the manipulating handle. One end of the manipulating handle is provided with a connecting port, the oocyte denuding pipette is connected to the connecting port; the drive module includes a micro-cylinder module, a transmission mechanism and a stepper motor; the control module includes a stepper motor driver, a single-chip microcomputer and a key module; the stepper motor driver, the key module, a display module, the power module and the memory are respectively connected to the single-chip microcomputer; the stepper motor driver is connected to the stepper motor; the stepper motor is connected to the transmission mechanism, and the transmission mechanism is connected to a micro-pushrod; another end of the micro-pushrod is arranged in a micro-cylinder, the micro-cylinder is in communication with a sealing tube of the oocyte denuding pipette; and the bulb is in communication with the oocyte denuding pipette.

The electric oocyte denuding device according to the present application is further configured as follows. The oocyte denuding pipette is an oocyte denuding pipette tip, an oocyte denuding needle or an oocyte denuding Pasteur pipette.

The electric oocyte denuding device according to the present application is further configured as follows. A start-stop key, an accelerator key and a decelerator key are provided on the manipulating handle, and are electrically connected to the key module respectively.

The electric oocyte denuding device according to the present application is further configured as follows. A drive module bin and a main bin are provided in the manipulating handle; the drive module is received in the drive module bin; the control module and the power module are received in the main bin; and a display screen is further embedded in the manipulating handle.

The electric oocyte denuding device according to the present application is further configured as follows. A central hole is provided at a center of the connecting port, a tail end of the central hole is narrowed to form a stop ring; the central hole is configured to receive the sealing tube, and the sealing tube is limited inside the central hole by the stop ring, and an outer wall of the sealing tube fits closely against an inner wall of the central hole; an opening at one end of the sealing tube is provided with a coupling configured to be in a tight plug-in connection with the oocyte denuding pipette; and an opening at another end of the sealing tube is provided with a coupling configured to be in a tight connection with a hose in communication with the micro-cylinder, a coupling configured to be in a tight connection with a hose in communication with the bulb, and a coupling configured to be in a tight connection with a hose connected to the pressure sensor.

The electric oocyte denuding device according to the present application is further configured as follows. The micro-cylinder module includes the micro-cylinder, the sealing tube, a pressing member and a pressing nut, wherein the micro-pushrod is connected to the micro-cylinder; the sealing tube is received in the micro-cylinder, the pressing member fits closely against the sealing tube, the pressing nut is connected to the micro-cylinder by screw threads, the pressing member has a part located inside the pressing nut and another part protruding from a circular opening of the pressing nut.

The electric oocyte denuding device according to the present application is further configured as follows. The transmission mechanism includes a screw rod and a nut-slider. The screw rod is connected to the stepper motor, and one end of the micro-pushrod is fixed to the nut-slider.

The electric oocyte denuding device according to the present application is further configured as follows. The transmission mechanism includes a spur gear and a spur rack-slider. The spur gear is assembled on the stepper motor, and one end of the micro-pushrod is fixed to the spur rack-slider.

The electric oocyte denuding device according to the present application is further configured to include a voice module which is connected to the single-chip microcomputer.

The electric oocyte denuding device according to the present application is further configured to include a control box which is connected to the manipulating handle by a cable.

The electric oocyte denuding device according to the present application is further configured as follows. A display screen is provided on the control box, or each of the manipulating handle and the control box is provided with a display screen.

The electric oocyte denuding device according to the present application is further configured to include a pressure sensor, wherein the pressure sensor is also connected to the single-chip microcomputer, and a pressure sensing element of the pressure sensor is in communication with the oocyte denuding pipette by a pipeline.

To achieve the above second object, the technical solution adopted in the present application is as follows. An oocyte denuding method includes the following steps: transferring an oocyte-corona-cumulus complex into a solution of hyaluronidase by a Pasteur pipette which is not drawn, continuously blowing and striking the oocyte-corona-cumulus complex for a plurality of times to remove most of mucus clots, and then transferring the predigested oocyte-corona-cumulus complex into an operational culture medium, driving the predigested oocyte-corona-cumulus complex to repeatedly enter and exit from an orifice of the oocyte denuding pipette by a power for blowing and suctioning provided by the stepper motor until a granular cell removal degree meets an operational requirement.

In the oocyte denuding method according to the present application, the stepper motor is controlled by the single-chip microcomputer and includes at least three velocity adjustment modes: alternately using pre-stored programs to adjust a velocity; manually increasing or decreasing a frequency value on the basis of a blowing/suctioning frequency of a running program, wherein a magnitude of increasing or decreasing the frequency value in a single operation is settable by programming; and automatically increasing a blowing/suctioning frequency to a certain set high value on the basis of the blowing/suctioning frequency of the running program, and maintaining at the set high value for a set duration, and then restoring to an original blowing/suctioning frequency.

To achieve the above second object, another technical solution adopted in the present application is as follows. An oocyte denuding method includes the following steps: in a case that oocyte denudation is performed after IVF using test tube method, transferring a suspension liquid of cultural medium of an oocyte-corona-cumulus complex to an empty culture dish by a Pasteur pipette which is not drawn, driving the oocyte-corona-cumulus complex to repeatedly enter and exit from an orifice of the oocyte denuding pipette by a power for blowing and suctioning provided by the stepper motor until a granular cell removal degree meets an operational requirement; and in a case that oocyte denudation is performed after IVF using micro drop method, repeatedly blowing and suctioning an oocyte adhered to a bottom of a culture dish along with granular cells by a power for blowing and suctioning provided by the stepper motor, to separate the oocyte and the granular cells from the bottom of the culture dish, and then repeatedly blowing and suctioning the oocyte until a granular cell removal degree meets an operational requirement.

In the oocyte denuding method according to the present application, the stepper motor is controlled by the single-chip microcomputer and includes at least three velocity adjustment modes: alternately using pre-stored programs to adjust a velocity; manually increasing or decreasing a frequency value on the basis of a blowing/suctioning frequency of a running program, wherein a magnitude of increasing or decreasing the frequency value in a single operation is settable by programming; and automatically increasing a blowing/suctioning frequency to a certain set high value on the basis of the blowing/suctioning frequency of the running program, and maintaining at the set high value for a set duration, and then restoring to an original blowing/suctioning frequency.

Compared with the conventional technology, the present application has the following beneficial effects.

1. Precise positioning, safe and effective. The oocyte denuding operation without generating bubbles not only shortens the operation time, but also avoids losing oocytes, and is controlled accurately, thus preventing the temperature of the culture medium where the oocytes are located from having significant fluctuations, and, to the maximum degree, reducing the damage to the oocytes caused by temperature fluctuations, and having a positive significance in improving the pregnancy outcome.

2. The oocyte denuding process has quantified indexes, thus reducing the effects of subjective factors, and the oocyte denuding operation records can be stored and looked up, thus addressing the issues in the conventional oocyte denuding technology that the oocyte denuding operations cannot be compared between different operators and the past operations of the same operator cannot be reviewed and analyzed, and having an important significance in achieving standardization of the oocyte denuding operation.

3. High degree of automation. The oocyte denudation may be performed according to set programs by simply pressing the start-stop button, and the manual acceleration and deceleration can be conveniently achieved by the accelerator key and the decelerator key, and the automatic velocity adjustment may realize automatic acceleration and then restore to the original velocity. The control is simple, and the operation is easy, and compared with the conventional oocyte denuding method, the oocyte denuding method of the present application has a remarkable significance in reducing the labor intensity.

BRIEF DESCRIPTION OF THE DRAWINGS

FIG. 2-1 is a schematic view of an oocyte denuding pipette tip;

FIG. 2-2 is a schematic view of an oocyte denuding needle;

FIG. 2-3 is a schematic view of an oocyte denuding Pasteur pipette;

FIG. 3-1-1 is an exploded view of a manipulating handle of an integrated type electric oocyte denuding device according to the present application;

FIG. 3-1-2 is a partial view of a connecting port and a sealing tube in FIG. 3-1-1;

FIG. 3-2 is a perspective view of a manipulating handle and a control box of a separated type electric oocyte denuding device according to the present application;

FIG. 4-1-1 is an exploded view of a manipulating handle of an integrated type electric oocyte denuding device according to the present application;

FIG. 4-1-2 is a partial view of a connecting port and a sealing tube in FIG. 4-1-1;

FIG. 4-2 is a perspective view of a manipulating handle and a control box of a separated type electric oocyte denuding device according to the present application;

FIG. 5-1-1 is an exploded view of a micro-cylinder module of the electric oocyte denuding device according to the present application;

FIG. 5-1-2 is an exploded view of another form of the micro-cylinder module of the electric oocyte denuding device according to the present application;

FIG. 5-2 is a perspective view of a drive module of the electric oocyte denuding device according to the present application;

FIG. 5-3 is a perspective view of another form of the drive module of the electric oocyte denuding device according to the present application;

FIG. 6-1 shows the integrated type electric oocyte denuding device according to the present application connected with the oocyte denuding pipette tip;

FIG. 6-2 shows the integrated type electric oocyte denuding device according to the present application connected with the oocyte denuding needle;

FIG. 6-3 shows the integrated type electric oocyte denuding device according to the present application connected with the oocyte denuding Pasteur pipette;

FIG. 7-1 shows the separated type electric oocyte denuding device according to the present application connected with the oocyte denuding pipette tip;

FIG. 7-2 shows the separated type electric oocyte denuding device according to the present application connected with the oocyte denuding Pasteur pipette.

DETAILED DESCRIPTION

Figure 1:
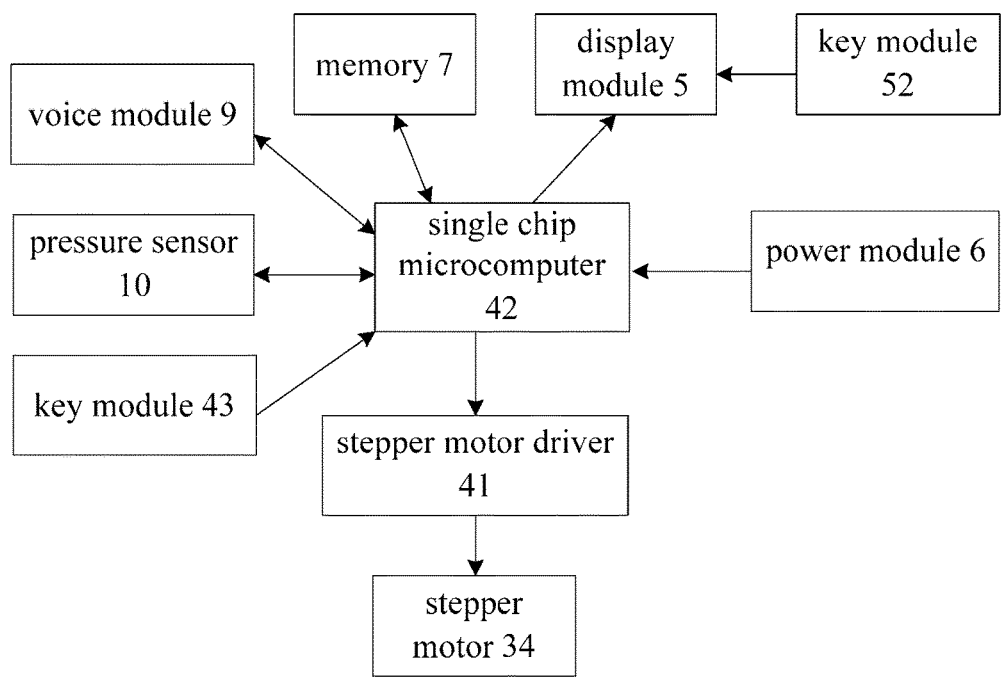
FIG. 1 is a schematic view showing the principle of an electric oocyte denuding device according to the present application.

Reference is made to FIGS. 1 to 8 of the specification, an electric oocyte denuding device is provided according to the present application, which includes an oocyte denuding pipette 1, a manipulating handle 2, a drive module 3, a control module 4, a display module 5, a power supply module 6, a memory 7, a bulb 8, and/or a voice module 9, and/or a pressure sensor 10, and/or a control box 11 and etc.

The electric oocyte denuding device can be held by one hand in a writing posture, specifically, a thumb and an index finger grip a thin portion formed by a tail end of the manipulating handle 2 extending downward and narrowing, and a middle finger assists in holding the device, and the manipulating handle 2 is supported on the thumb-index web space.

Figures 1, 2:
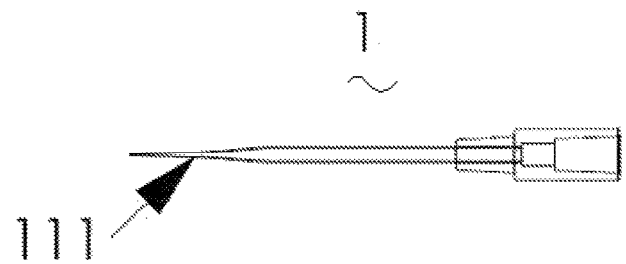
Figure 2:
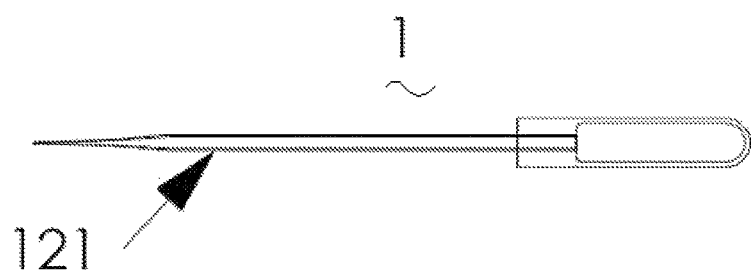
Figures 2, 3:
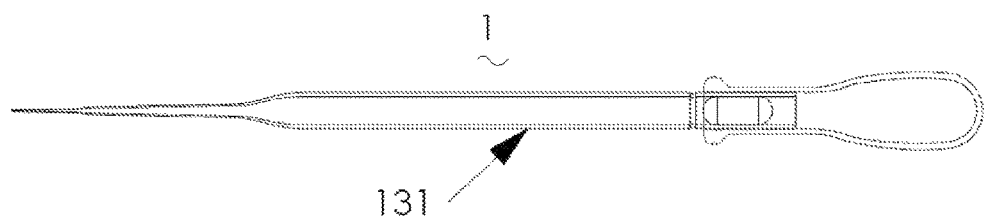
Figures 1, 3:
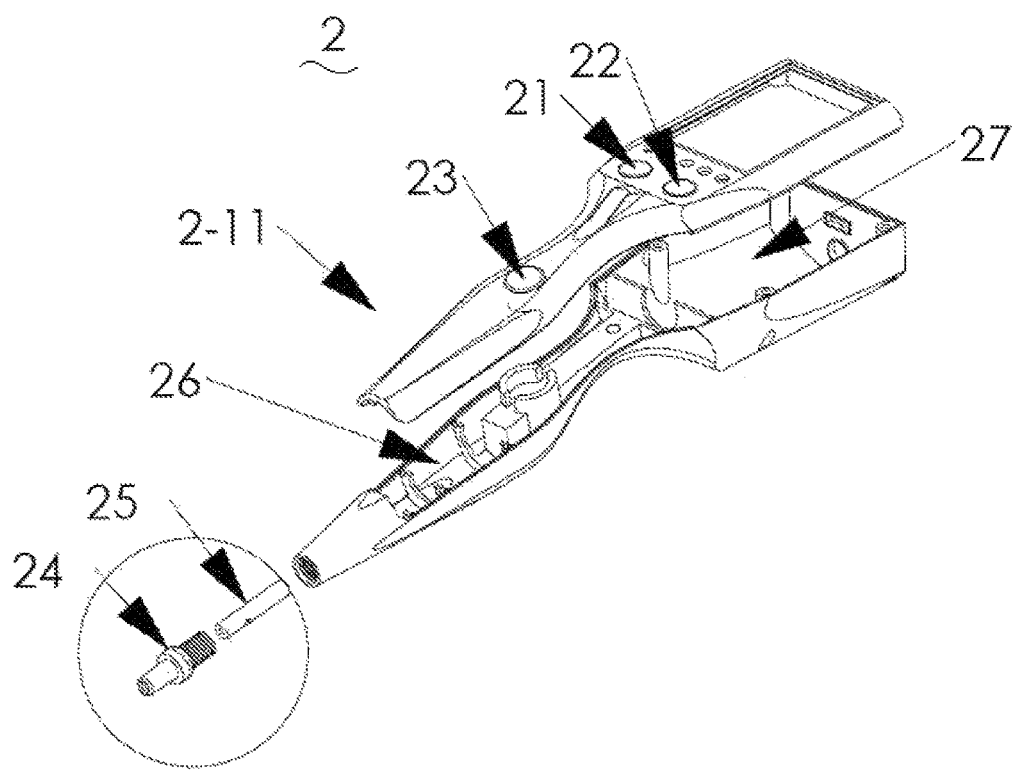
Figures 1, 2, 3:
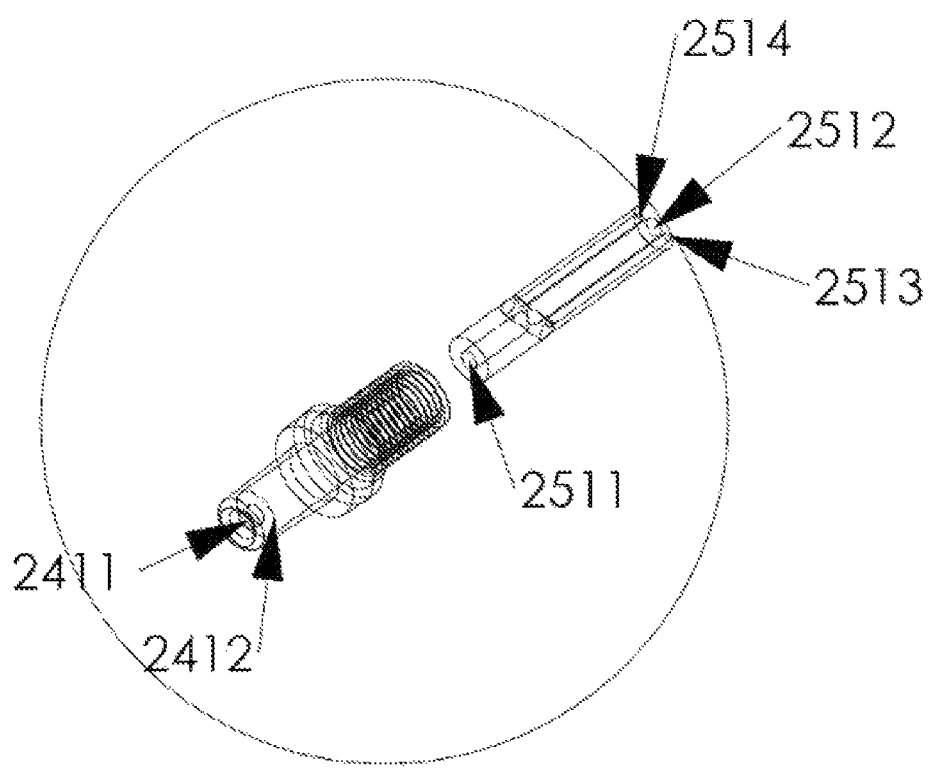
Figures 2, 3:
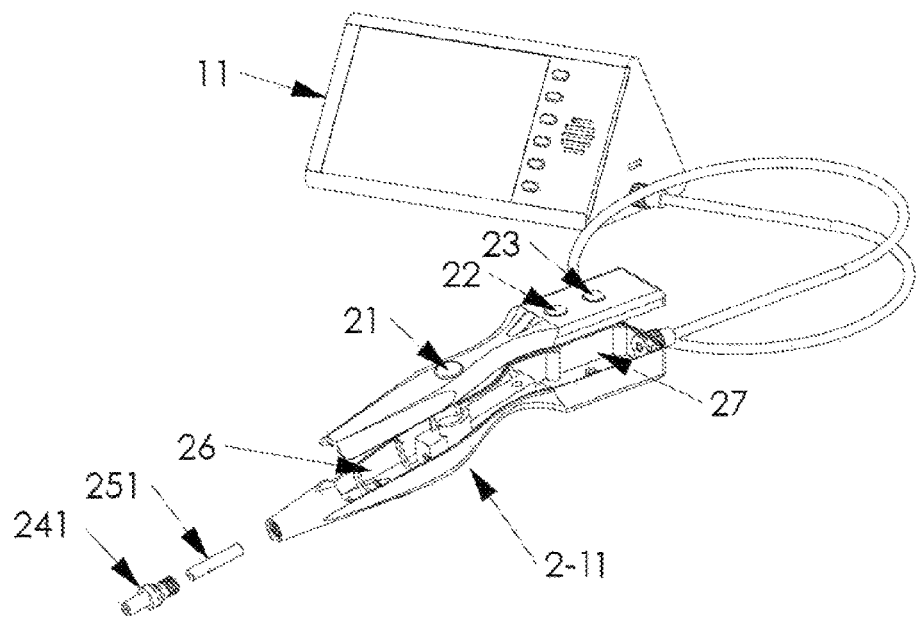

As shown in FIGS. 2-1 to 2-3, the oocyte denuding pipette 1 may be embodied as an oocyte denuding pipette tip 111, an oocyte denuding needle 121, or an oocyte denuding Pasteur pipette 131. The oocyte denuding pipette 1 is a plug-and-play operating element, and is a disposable instrument for avoiding cross-contamination between samples.

As shown in FIGS. 3-1-1 to 4-2, the manipulating handle 2 is provided with a start-stop key 21, an accelerator key 22, a decelerator key 23, a connecting port 24, a sealing tube 25, a drive module bin 26, a main bin 27, and a panel. The manipulating handle 2 constitutes a main part of a housing of the electric oocyte denuding device. The drive module bin 26 is mainly configured to accommodate the drive module 3. The main bin 27 is mainly configured to accommodate the control module 4, the display module 5, the power supply module 6, the memory 7, the bulb 8, and/or the voice module 9, and/or the pressure sensor 10 and etc. The panel is mainly configured to arrange the keys, buttons and/or interfaces.

Figures 1, 4:
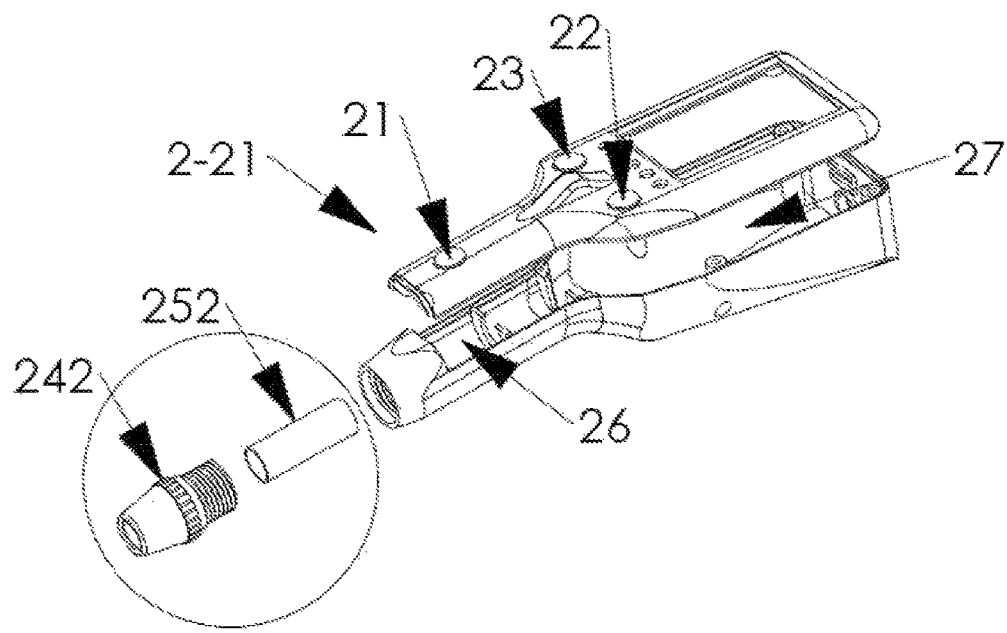
Figures 1, 2, 4:
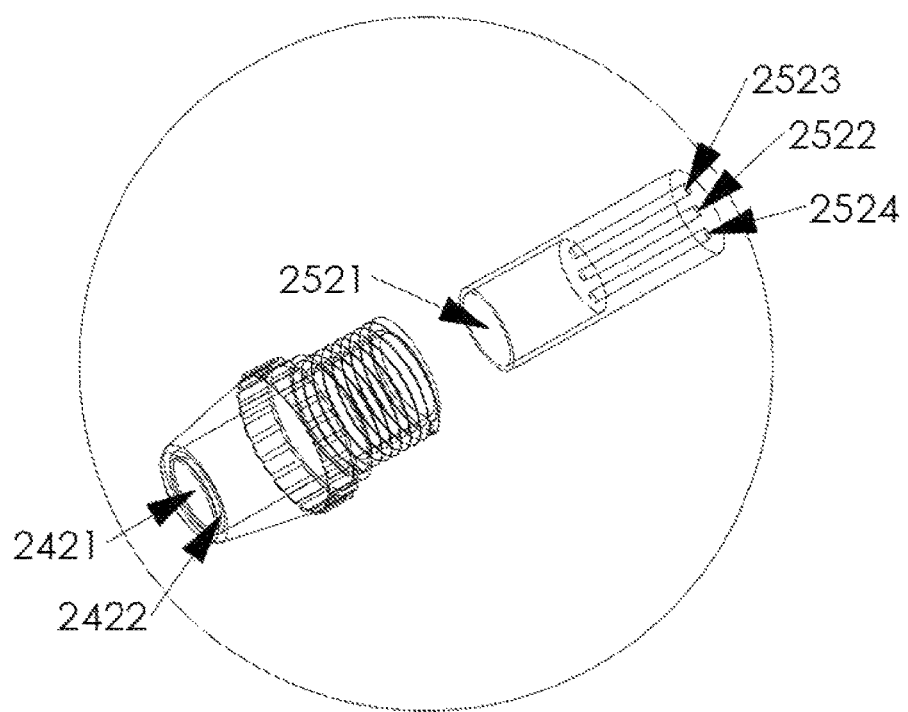
Figures 2, 4:
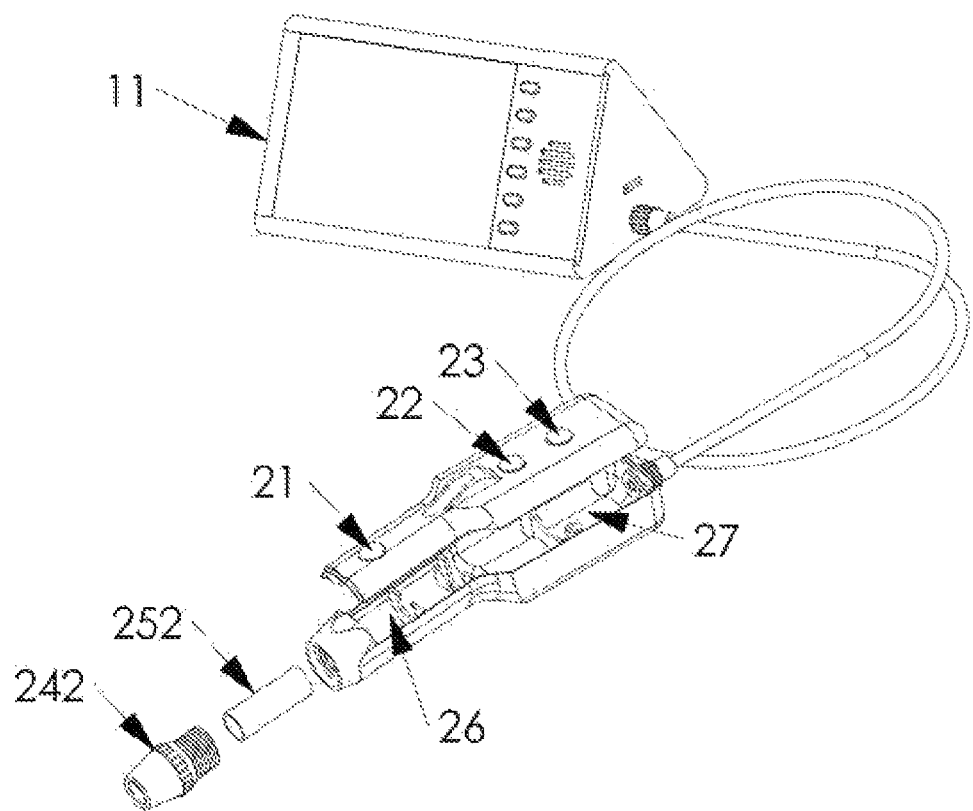

The manipulating handle 2 may be designed to have different variants according to different oocyte denuding pipettes 1 to which the manipulating handle 2 is connected, such as a manipulating handle 2-11 adapted to the oocyte denuding pipette tip 111 and the oocyte denuding needle 121, as shown in FIGS. 3-1-1 and 3-2, and a manipulating handle 2-21 adapted to the oocyte denuding Pasteur pipette 131, as shown in FIGS. 4-1-1 and 4-2.

The panel of the manipulating handle 2 is provided with one start-stop key 21. The start-stop key 21 is connected to a key, having a program starting and stopping function, of a key module 43 by a flexible electric wire.

The start-stop key 21 protrudes from a curved surface, through which the finger pulp of the thumb passes when the thumb in a holding state naturally swings, of the manipulating handle 2. The protruding position of the start-stop key 21 may be arranged toward a left side of a gripping section of the manipulating handle 2 to facilitate the use of right-handers, or may be arranged toward a right side of the gripping section of the manipulating handle 2 to facilitate the use of left-handers, and may further be arranged on a straight front side of the gripping section of the manipulating handle 2, to facilitate the use of both the right-handers and the left-handers. Preferably, the protruding position of the start-stop key 21 is provided on the straight front side of the gripping section of the manipulating handle 2.

The panel of the manipulating handle 2 is provided with one accelerator key 22 and one decelerator key 23. The accelerator key 22 is connected to a key, having acceleration function, of the key module 43 by a flexible electric wire, and the decelerator key 23 is connected to a key, having deceleration function, of the key module 43 by a flexible electric wire. The protruding positions of the accelerator key 22 and the decelerator key 23 are provided toward the left side, or the right side, or the straight front side of the manipulating handle 2. Preferably, the protruding positions of the accelerator key 22, the decelerator key 23 and the start-stop key 21 are arranged on the same longitudinal curved surface. Preferably, the protruding positions of the accelerator key 22 and the decelerator key 23 are arranged on the straight front side of the panel at a head end of the manipulating handle 2.

The shapes, sizes, materials and protruding heights of keycaps of the start-stop key 21, the accelerator key 22 and the decelerator key 23 are set to meet the requirement for capable being flexibly operated by fingers of most people. Preferably, keycaps of different shapes, sizes and materials may be selected according to personal preference.

The thumb of the hand gripping the electric oocyte denuding device is used to control the start-stop key 21, the accelerator key 22 and the decelerator key 23, and/or the other hand is used to assist in controlling the accelerator key 22 and the decelerator key 23.

The connecting port 24 is connected to a main body of the manipulating handle 2 through a threaded coupling. The manipulating handle 2 and the oocyte denuding needle 1 are in a tight plug-in connection by the connecting port 24. The connecting port 24 may be designed to have different variants according to different oocyte denuding pipettes 1 to which the connecting port 24 is connected, such as a connecting port 241 adapted to the oocyte denuding pipette tip 111 and the oocyte denuding needle 121, as shown in FIGS. 3-1 and 3-2, and a connecting port 242 adapted to the oocyte denuding Pasteur pipette 131, as shown in FIGS. 4-1 and 4-2.

As shown in FIGS. 3-1-1 and 3-1-2, a central longitudinal axis of the connecting port 241 is a central hole 2411, and a tail end of the central hole 2411 is narrowed to form a stop ring 2412. A sealing tube 251 is accommodated in the central hole 2411, and the sealing tube 251 is made of an elastic material such as rubber, latex, silica gel or the like. The sealing tube 251 is limited inside the central hole 2411 by the stop ring 2412, an outer wall of the sealing tube 251 closely fits against an inner wall of the central hole 2411, and a strict air tightness is formed therebetween. An opening, towards the stop ring 2412, of the sealing tube 251 is provided with a coupling 2511 which is in a tight plug-in connection with the oocyte denuding needle 121, and the port 241 has a connecter 2413 which is in a tight plug-in connection with a needle seat of the oocyte denuding pipette tip 111. An opening, away from the stop ring 2412, of the sealing tube 251 is provided with a coupling 2512 which is in a tight connection with a hose in communication with a micro-cylinder 311 or is in a tight connection with the micro-cylinder 311, and is further provided with a coupling 2513 which is in a tight connection with a hose in communication with the bulb 8, and/or a coupling 2514 which is in a tight connection with a hose connected to the pressure sensor 10.

As shown in FIGS. 4-1-1 and 4-1-2, a central longitudinal axis of the connecting port 242 is a central hole 2421, and a tail end of the central hole 2421 is narrowed to form a stop ring 2422. A sealing tube 252 is accommodated in the central hole 2421, and the sealing tube 252 is made of an elastic material such as rubber, latex, silica gel or the like. The sealing tube 252 is limited inside the central hole 2421 by the stop ring 2422, an outer wall of the sealing tube 252 closely fits against an inner wall of the central hole 2421, and a strict air tightness is formed therebetween. An opening, toward the stop ring 2422, of the sealing tube 252 is provided with a coupling 2521 which is in a tight plug-in connection with a tail end of the oocyte denuding Pasteur pipette 131. An opening, away from the stop ring, of the sealing tube 252 is provided with a coupling 2522 which is in a tight connection with a hose in communication with the micro-cylinder 311 or is in a tight connection with the micro-cylinder 311, and is further provided with a coupling 2523 which is in a tight connection with a hose in communication with the bulb 8, and/or a coupling 2524 which is in a tight connection with a hose connected to the pressure sensor 10.

The drive module 3 includes a micro-cylinder module 31, a sliding groove 32, a transmission mechanism 33, and a stepper motor 34.

Figures 1, 5:
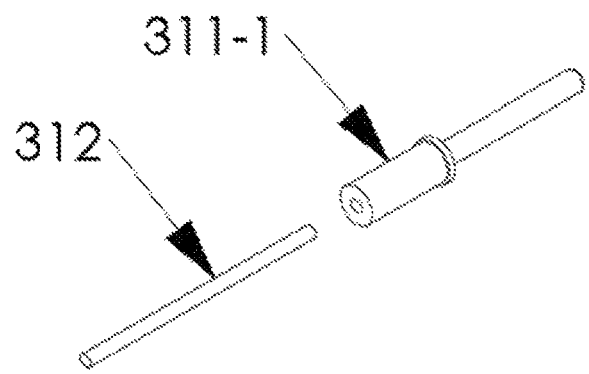
Figures 1, 2, 5:
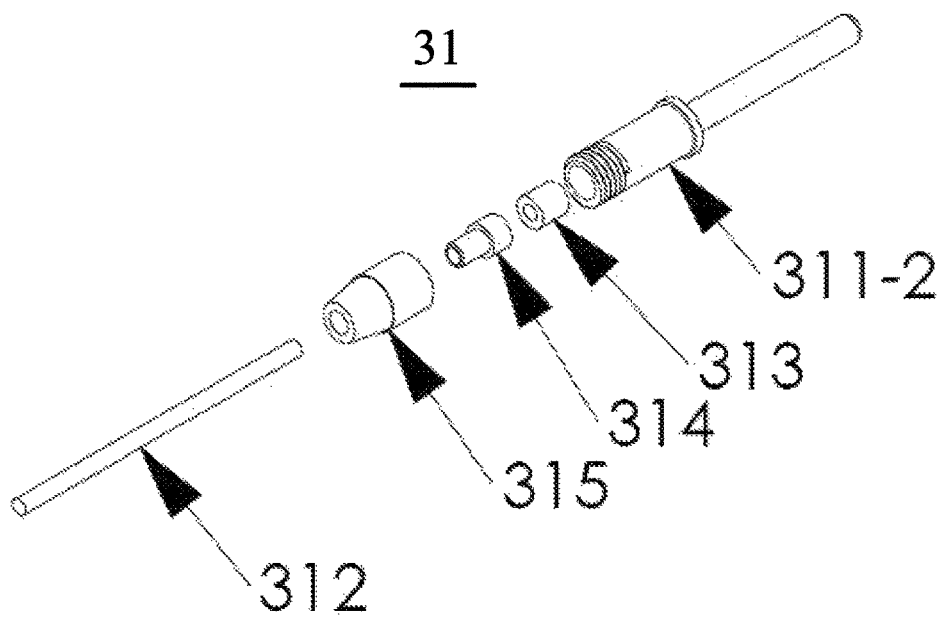
Figures 2, 5:
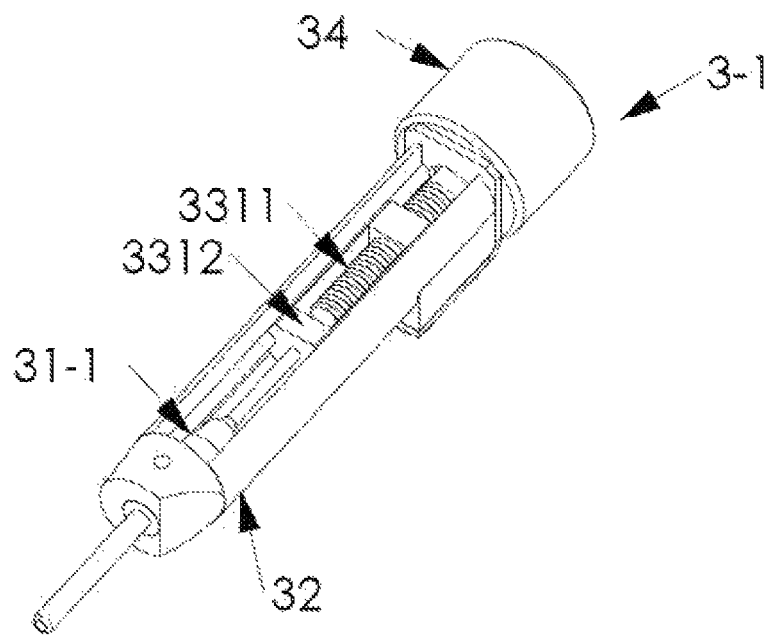
Figures 3, 5:
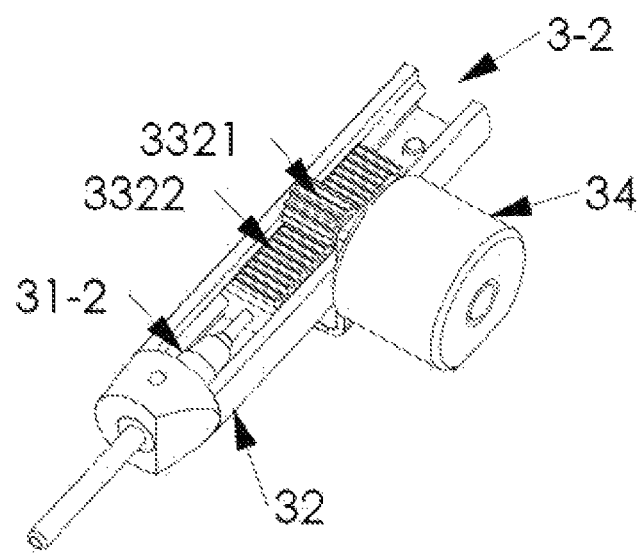
Figures 1, 6:
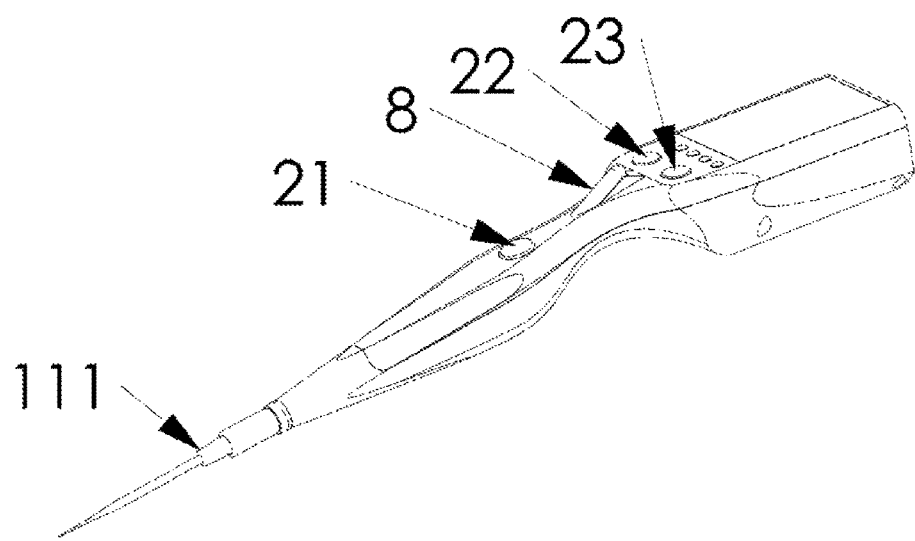
Figures 2, 6:
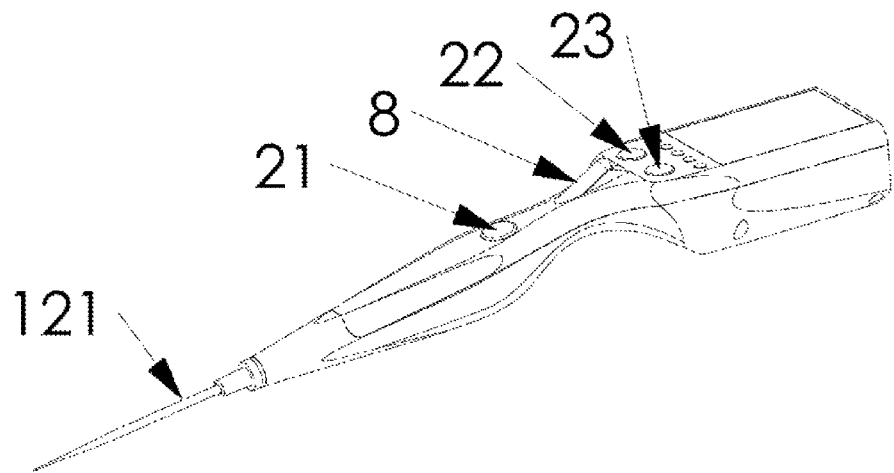
Figures 3, 6:
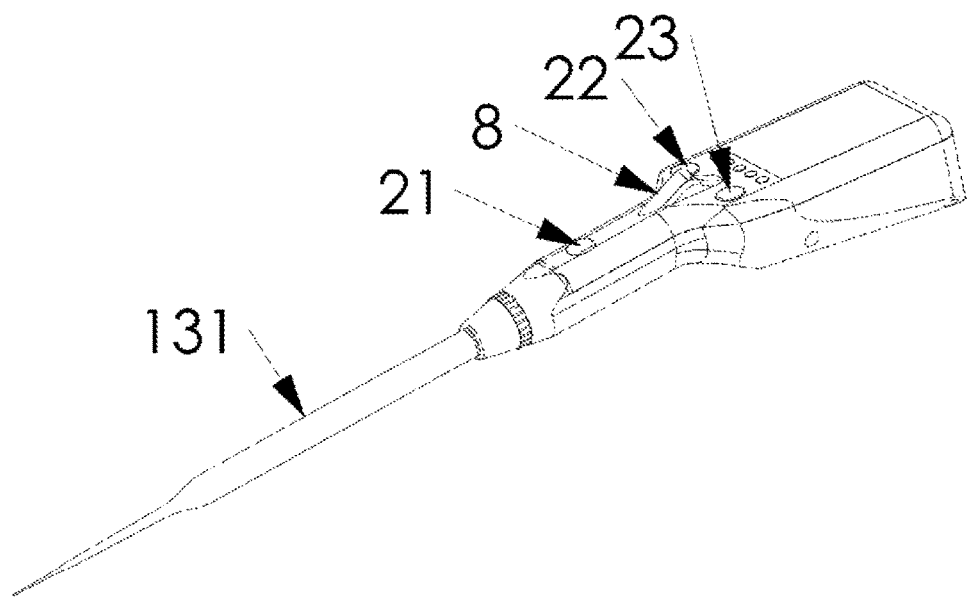
Figures 1, 7:
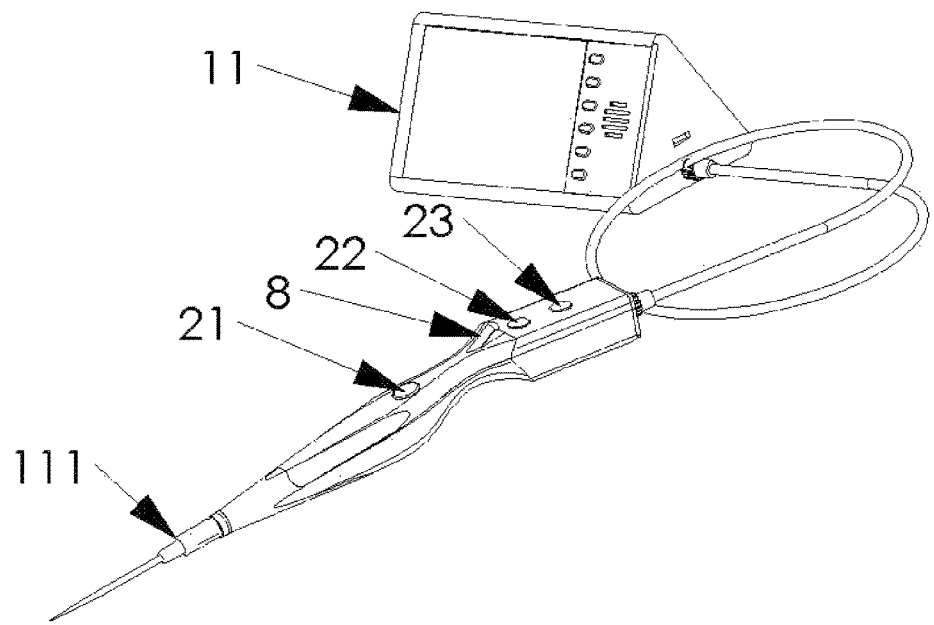
Figures 2, 7:
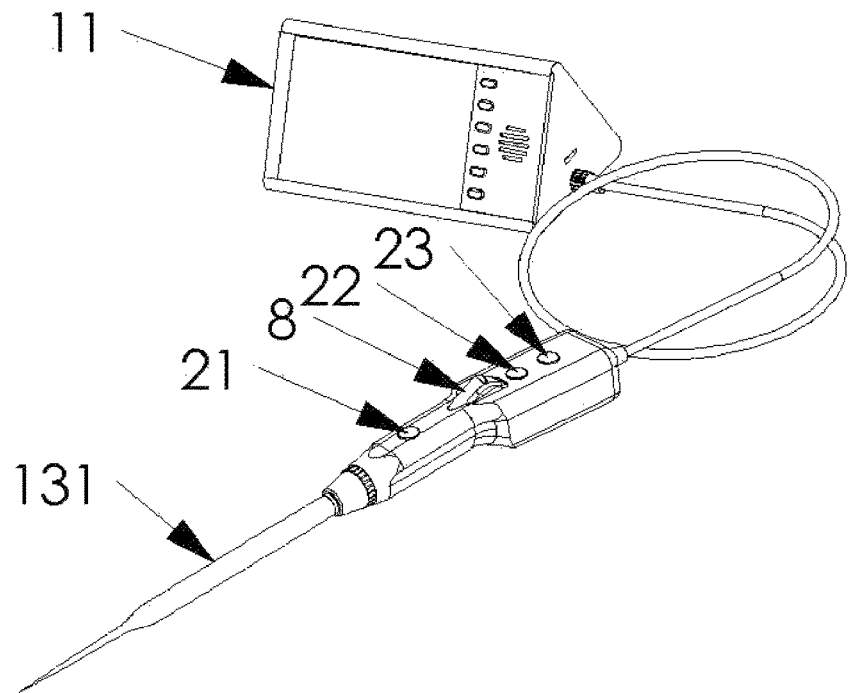
Figure 8:
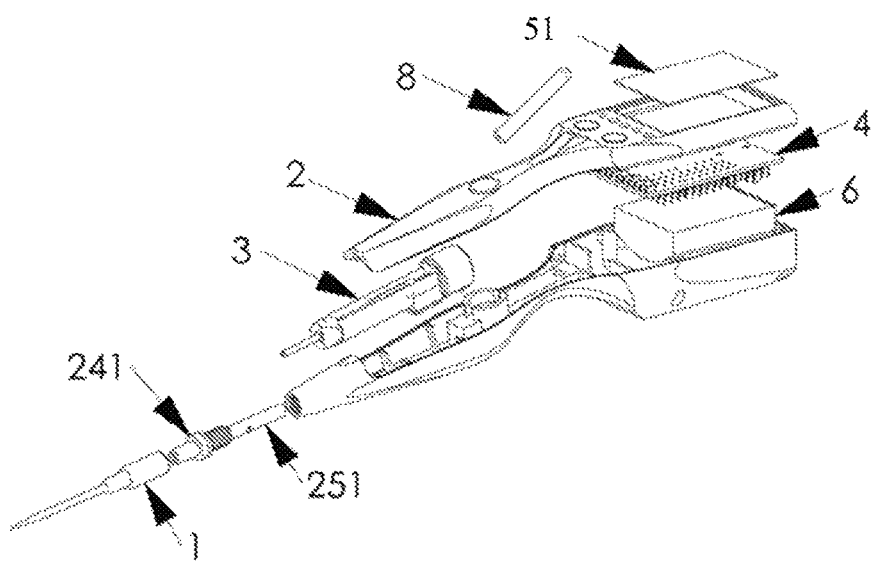
FIG. 8 is an exploded perspective view of the electric oocyte denuding device according to the present application.

As shown in FIGS. 5-1-1 and 5-1-2, the micro-cylinder module 31 includes a micro-cylinder 311, a micro-pushrod 312, and/or a sealing tube 313, and/or a pressing member 314, and/or a pressing nut 315. The micro-cylinder 311 may be a micro-cylinder 311-1 having a simple round tubular structure, and may also be a micro-cylinder 311-2 improved on the basis of the micro-cylinder 311-1. As shown in FIG. 5-2, an outer wall of the micro-pushrod 312 and the micro-cylinder 311-1 may constitute the micro-cylinder module 31-1 having a simple structure, and the outer wall of the micro-pushrod 312 and an inner wall of the micro-cylinder 311-1 has a strict air tightness formed therebetween and while having a small frictional force therebetween. As shown in FIG. 5-1, an inner diameter of the central hole, at an end where the micro-pushrod 312 is located, of the micro-cylinder 311-1 is increased to form a circular cavity, and an outer wall corresponding to the circular cavity has a screw thread, thus forming the micro-cylinder 311-2. The sealing tube 313 is made of an elastic material such as rubber, latex, silica gel or the like. An inner diameter of the central hole of the sealing tube 313 is same as an outer diameter of the micro-pushrod 312, and an outer diameter of the sealing tube 313 is same as an inner diameter of the circular cavity of the micro-cylinder 311. The pressing member 314 is a hollow metal cylinder including a thick section and a thin section, an inner diameter of a center hole of the pressing member 314 is greater than the outer diameter of the micro-pushrod 312, and an outer diameter of the thick section of the pressing member 314 is same as the inner diameter of the circular cavity of the micro-cylinder 311-2 and is greater than an inner diameter of a circular opening of the pressing nut 315 at an end opposite to a threaded coupling of the pressing nut 315, and an outer diameter of the thin section of the pressing member 314 is same as the inner diameter of the circular opening of the pressing nut 315 at the end opposite to the threaded coupling of the pressing nut 315. The pressing nut 315 is a hollow irregular-shaped nut having the threaded opening at one end and the circular opening at the opposite end. The sealing tube 313 is accommodated inside the circular cavity of the micro-cylinder 311-2, and the thick section of the pressing member 314 closely fits against the sealing tube 313. After the pressing nut 315 is connected to the micro-cylinder 311-2 by screw threads, the thick section and a part of the thin section of the pressing member 314 are located inside the pressing nut 315, and the rest part of the thin section of the pressing member 314 extends out of the circular opening of the pressing nut 315. As shown in FIG. 5-2, the micro-pushrod 312 is inserted into the micro-cylinder 311-2 after passing through the central hole of the pressing member 314 and the central hole of the sealing tube 313, thus forming the micro-cylinder module 31-2. The pressing nut 315 presses the sealing tube 313 through the pressing member 314, to deform the sealing tube 313. By adjusting the length of the engaged thread of the threaded connection between the pressing nut 315 and the micro-cylinder 311-2, the degree of radial deformation of the sealing tube 313 can be adjusted, and further the air tightness and the frictional force between the sealing tube 313 and the micro-pushrod 312 can be adjusted.

As shown in FIGS. 5-2 and 5-3, the transmission mechanism 33 in the drive module 3 can be embodied as the following two forms according to the principle, including a transmission mechanism using a screw rod 3311 and a nut-slider 3312 as main transmission components, and a transmission mechanism using a spur gear 3321 and a spur rack-slider 3322 as main transmission components. One of the two forms is selected as the transmission mechanism of the electric oocyte denuding device.

As shown in FIG. 5-2, in the structure of the transmission mechanism, the nut and the slider are designed integrally, and the screw rod 3311 is an output section of a rotating shaft of the stepper motor 34. The sliding groove 321 may fix both the stepper motor 34 and the micro-cylinder module 31. One end of the micro-pushrod 312 is fixed on the nut-slider 3312. The stepper motor 34, the sliding groove 321, the nut-slider 3312, and the micro-cylinder module 31 as a whole constitute the drive module 3-1, which facilitates assembly and saves space.

As shown in FIG. 5-3, in the structure of the transmission mechanism, the spur rack and the slider are designed integrally, and the spur gear 3321 is assembled on the output section of the rotating shaft of the stepper motor 34. The sliding groove 322 may fix both the stepper motor 34 and the micro-cylinder module 31. One end of the micro-pushrod 312 is fixed to the spur rack-slider 3322. The stepper motor 34, the sliding groove 322, the spur rack-slider 3322, and the micro-cylinder module 31 as a whole constitute the drive module 3-2, which facilitates assembly and saves space.

The transmission mechanism 33 functions to convert the forward and reverse rotations of the stepper motor 34 into a linear reciprocating movement of the micro-pushrod 312. In the drive module 3-1, a step angle of the stepper motor 34 and a pitch of the screw rod 3411 determine a linear stroke of the stepper motor 34 at a single pulse. In the drive module 3-2, the step angle of the stepper motor 34 and the diameter of a pitch circle of the spur gear 3421 determine a linear stroke of the stepper motor 34 at a single pulse. The physical parameters of the transmission mechanism 33, such as the pitch and the lead of the screw rod and the diameter of the pitch circle of the spur gear, and the step angle of the stepper motor 34 can meet the requirement of adjusting the length of the liquid column in an oocyte denuding procedure.

The stepper motor 34 in the drive module 3 is preferably embodied as a two-phase four-wire stepper motor, and in order to allow the electric oocyte denuding device to be lighter, the stepper motor 34 is preferably embodied to have a smaller size and a lower power consumption on the premise of meeting the requirement for performing the oocyte denuding procedure.

The drive module 3 is arranged inside the drive module bin 26 of the manipulating handle 2. For the separated-type electric oocyte denuding device, the drive module 3 may also be arranged inside the control box 11.

The control module 4 includes a stepper motor driver 41, a single chip microcomputer 42, and a key module 43. The stepper motor driver 41, the single chip microcomputer 42 and the key module 43 may be embodied as an integrated circuit module.

The key module 43 includes at least keys or electrical connection points having functions of program selecting, starting and stopping, accelerating, decelerating, stroke increasing, and stroke decreasing. Preferably, different functions may be combined in one key to be implemented, for example, different functions may be performed by pressing twice the same key continuously, different functions may be performed by pressing the same key for different durations, and different functions may be performed by pressing the same key successively for different number of times, and so on.

The keys of the key module 43 may be button keys or touch screen keys or the like.

The display module 5 includes a display screen 51 and a key module 52. The display screen 51 is configured to display basic parameters of the running program, such as a program number, a blowing/suctioning frequency, a length of liquid column, and/or operating data such as a real-time blowing/suctioning frequency, a start time and an end time of a certain blowing/suctioning frequency, an accumulated operation time at a certain blowing/suctioning frequency, a total operation time, and/or an electric quantity of a battery or an accumulator, and/or an alarm, and etc. The display screen 51 may be embodied as an LED display screen, or an LCD display screen, or a touch display screen, and supports multi-language display. The languages include at least Chinese and English or the like. The display screen 51 can be a black and white display screen or color display screen.

The display screen 51 is mounted on a straight front side of the panel at the head end of the manipulating handle 2, or on a lateral side, where a thumb of a hand gripping the manipulating handle 2 is located, of the panel at the head end of the manipulating handle 2, and/or a straight front side of the control box 11.

Depending on different installation positions, the display screen 51 with an appropriate size and resolution is selected and appropriate display contents are selected. If the display screen 51 is only mounted on the panel at the head end of the manipulating handle 2, a display screen having a high resolution is preferably employed, and the size of the display screen 51 is required to meet the requirements of lightweight and aesthetic for the whole electric oocyte denuding device while meeting the requirements for displaying basic parameters of the running programs.

If each of the manipulating handle 2 and the control box 11 is provided with the display module 5, it is preferable that the display screen 51 on the manipulating handle 2 only requires a display screen having a small size and a relatively low resolution while the display screen 51 on the control box 11 requires a display screen having a larger size and a high resolution, thereby meeting the requirement for allowing the operator to clearly recognize the contents on the display screens in a dark field of view within 1 meter of sighting distance. The display screen 51 is preferably configured to have a lower power consumption on the premise of meeting the above conditions.

The keys of the key module 52 may be embodied as button keys or touch screen keys or the like. The key module 52 has functions corresponding to the displayer 51. Preferably, part of the keys of the key module 52 and the keys of the key module 43 of the control module 4 are combined to reduce the number of the keys as small as possible and to allow the operation interface to be simple.

The power supply module 6 includes a charging module 61 and an electric energy storage unit 62. The charging module 61 is used to charge the electric energy storage unit. The electric energy storage unit is an accumulator or a battery similar to a lithium ion battery. The charging module 61 and the electric energy storage unit 62 are preferably configured to have a small size and a light weight on the premise of satisfying the normal power consumption demand of the electric oocyte denuding device.

The power supply module 6 is arranged inside the main bin 27 of the manipulating handle 2 or inside the control box 11.

The memory 7 is configured to store program running data, including information of an operation object such as numbering and the like, and data in the oocyte denuding operation corresponding to the operation object such as a program numbering, a blowing/suctioning frequency and a length of liquid column, and program running data such as a real-time blowing/suctioning frequency, a start time and an end time of a certain blowing/suctioning frequency, an accumulated operation time at a certain blowing/suctioning frequency, a total operation time and other data. In case that the memory 7 is electrically connected to the control module 4, the memory 7 is arranged inside a casing of the manipulating handle 2 or inside the control box 11.

The bulb 8 is in the shape of a cylinder or is shaped like a sphere, and is made of an elastic material such as rubber, latex, silica gel and the like. The bulb 8 is arranged on the gripping section of the manipulating handle 2. A connecting end of the bulb 8 is buried under the panel of the manipulating handle 2, and a blind end of the bulb 8 is exposed to the outside and is tilted at an angle, such as 30 degrees, towards the tail end of the manipulating handle 2. The connecting end of the bulb 8 is in communication with the oocyte denuding pipette 1 through a conduit. The position of the bulb 8 is arranged to cooperate with other operating elements on the manipulating handle 2, such as the start-stop key 21, the accelerator key 22 and the decelerator key 23. Preferably, the bulb 8 and the start-stop key 21 are adjacent to each other and are distributed longitudinally along the manipulating handle 2. The exposed portion of the bulb 8 is located at an outer end of the thumb of the hand gripping the electric oocyte denuding device, and the thumb can shift operation between the start-stop key 21 and the bulb 8 just by swinging naturally left and right. The maximum volumetric variable formed by pressing the bulb 8 with the thumb in the normal operating posture is an effective emptying volume of the bulb 8, and the effective emptying volume of the bulb 8 is less than the volume of the oocyte denuding needle 12 or the oocyte denuding pipette tip 111. The bulb 8 may be manipulated to perform operations on oocytes such as transferring oocytes.

The electric oocyte denuding device may further be provided with a voice module 9. During the oocyte denuding operation, the operator has both eyes or a single eye getting close to a microscope eyepiece to observe the oocyte denuding process. In order to avoid interruption of the oocyte denuding operation when the line of sight is diverted in the oocyte denuding process to observe the information on the display screen, certain information on the display screen such as the real-time blowing/suctioning frequency can be coded by acoustic coding and played through a speaker, and the operator may acquire the information through voice. The oocyte denuding operation is an in vitro operation on zygotic embryos, and has a strict limit on the in vitro operation time. Through programming by the single chip microcomputer, the total operation time and/or a timeout reminder can be informed to the operator by voice.

The voice module 9 is arranged in the main bin 27 of the manipulating handle 2 or in the control box 11.

The electric oocyte denuding device may further be provided with a pressure sensor 10. The pressure sensor 10 monitors pressure changes in a communicating pipeline between the micro-pushrod 312 and the oocyte denuding pipette 1 and transmits the pressure information to the single-chip microcomputer system. The single-chip microcomputer system automatically adjusts a pulse frequency for controlling the stepper motor according to the value of the pressure changes, to achieve the object of automatically adjusting the velocity. When an oocyte-corona-cumulus complex passes through a tip portion of the oocyte denuding needle 1 slowly due to being stuck there, a conventional oocyte denuding method is to accelerate the passage of the oocyte-corona-cumulus complex by increasing the suctioning force or the blowing force. However, the determination and handle to this situation by each operator are greatly affected by subjective factors, which does not facilitate the standardization. When an oocyte-corona-cumulus complex passes through the tip portion of the oocyte denuding needle 1 slowly due to being stuck there, the pressure in the communicating pipeline is lowered, and the value of the low pressure can be measured. An appropriate low pressure value can be selected as a threshold lower limit for programming. In the case that the pressure sensor 10 detects the threshold lower limit, a feedback is sent to the single-chip microcomputer 42, and the pulse frequency for controlling the stepper motor 34 is automatically increased to a set high value according to the program setting, thus increasing the blowing/suctioning frequency, and further increasing the blowing force and the suctioning force, to allow the oocyte-corona-cumulus complex to pass through the orifice of the oocyte denuding pipette 1 smoothly. After a predetermined number of times of blowing and suctioning at the set high pulse frequency are performed, the blowing/suctioning frequency is restored to the original blowing/suctioning frequency, thus achieving the object of automatically adjusting the blowing force and the suctioning force. Compared with the conventional oocyte denuding method in which the blowing/suctioning velocity is adjusted, the automatic adjustment of the blowing/suctioning frequency is triggered when the pressure in the communicating pipeline between the micro-pushrod 312 and the oocyte denuding pipette 1 is lower than the threshold lower limit, which is not affected by subjective factors of an operator and facilitates the standardization.

The pressure sensor 10 is arranged in the casing of the manipulating handle 2. An automatic velocity adjustment key for starting/closing this function is provided on the panel of the manipulating handle 2.

The control box 11 serves as a carrier for mounting other elements. In the case that the elements described above are physically separated from the manipulating handle 2, the separated elements are mounted in the control box 11, and corresponding keys, buttons and interfaces are provided on the panel of the control box 11.

As shown in FIG. 1, the connection relationships among the main elements of the electric oocyte denuding device are described as follows. The stepper motor driver 41, the key module 43, the display module 5, the power module 6, the memory 7, the voice module 9 and the pressure sensor 10 are respectively connected to the single-chip microcomputer 42, an output end of the stepper motor driver 41 is connected to the stepper motor 34, and a foot-operated switch controller 12 is in electrical connection with a corresponding key of the key module 43.

An output shaft of the stepper motor 34 is connected to an input end of the transmission mechanism 33, an output end of the transmission mechanism 33 is connected to one end of the micro-pushrod 312, and another end of the micro-pushrod 312 is arranged in the micro-cylinder 311. The micro-cylinder 311 is in communication with the oocyte denuding pipette 1 by a pipeline or is in direct communication with the oocyte denuding pipette 1 by the sealing tube 251 or by the sealing tube 252. The bulb 8 is in communication with the oocyte denuding pipette 1 by a pipeline, and a pressure sensing element of the pressure sensor 10 is in communication with the oocyte denuding pipette 1 by a pipeline. The manipulating handle 2 and the oocyte denuding pipette 1 are in a tight plug-in connection by the connecting port 24.

In addition to the tight detachable plug-in connection between the oocyte denuding pipette 1 and the manipulating handle 2, all the main components of the electric oocyte denuding device are fixedly assembled in the manipulating handle 2 to form an integrated type electric oocyte denuding device. Alternatively, in addition to the tight detachable plug-in connection between the oocyte denuding pipette 1 and the manipulating handle 2, the rest components are physically separated from the manipulating handle 2 and are fixedly assembled in the control box 11 to form a separated type electric oocyte denuding device. In the separated type electric oocyte denuding device, associated components are connected by flexible electric wires or flexible pipelines. The spatial layout of the main elements of the electric oocyte denuding device can be designed in the following five ways, and electric oocyte denuding devices with different shapes and similar functions can be achieved by the following five design ways.

In a first way, the oocyte denuding pipette 1 and the connecting port of the manipulating handle 2 are in a tight plug-in connection, and the drive module 3, the control module 4, the display module 5, the power module 6, the memory 7, the bulb 8, the voice module 9 and the pressure sensor 10 are mounted in the manipulating handle 2 to form an integrated type electric oocyte denuding device.

In a second way, the oocyte denuding pipette 1 and the connecting port of the manipulating handle 2 are in a tight plug-in connection, and the drive module 3, the control module 4, the display module 5, the memory 7, the bulb 8, the voice module 9 and the pressure sensor 10 are mounted in the manipulating handle 2, the power module 6 is mounted in the control box 11. A display module may further be mounted on the control box 11, and the display module is connected to the control module 4 by a flexible electric wire. The control box 11 is physically separated from the manipulating handle 2 to form a separated type electric oocyte denuding device. A foot-operated switch controller 12 physically separated from the elements described above may be further provided, and in this case, the start-stop key 21, the accelerator key 22 and the decelerator key 23 on the panel of the manipulating handle 2 can be kept or removed.

In a third way, the oocyte denuding pipette 1 and the connecting port of the manipulating handle 2 are in a tight plug-in connection, the drive module 3, the display module 5, the bulb 8, and the pressure sensor 10 are mounted in the manipulating handle 2, and the control module 4, the power module 6, the memory 7 and the voice module 9 are mounted in the control box 11. The display module 5 in the manipulating handle 2 is connected to the control module 4 by a flexible electric wire. Part of keys of the key module of the control module 4, such as keys for controlling starting, stopping, acceleration and deceleration, are connected to the start-stop key, the accelerator key and the decelerator key of the manipulating handle 2 by flexible electric wires. The pressure sensing element of the pressure sensor 10 is connected to the control module 4 by a flexible electric wire. The control box 11 is physically separated from the manipulating handle 2 to form a separated type electric oocyte denuding device. A foot-operated switch controller 12 physically separated from the elements described above may be further provided, and in this case, the start-stop key 21, the accelerator key 22 and the decelerator key 23 on the panel of the manipulating handle 2 can be kept or removed.

In a fourth way, the oocyte denuding pipette 1 and the connecting port of the manipulating handle 2 are in a tight plug-in connection, the display module 5, the bulb 8 and the pressure sensor 10 are mounted in the manipulating handle 2, and the drive module 3, the control module 4, the power module 6, the memory 7 and the voice module 9 are mounted in the control box 11. The display module 5 in the manipulating handle 2 is connected to the control module 4 by a flexible electric wire. A display module may be further mounted in the control box 11, and the display module is connected to the control module 4 by a flexible electric wire. Parts of the keys of the key module of the control module 4, such as keys for controlling starting, stopping, acceleration and deceleration, are connected to the start-stop key, the accelerator key and the decelerator key of the manipulating handle 2 by flexible electric wires. The micro-cylinder 311 in the drive module 3 is in communication with the oocyte denuding pipette 1 by a flexible pipeline, and the communicating pipeline between the micro-pushrod 312 and the oocyte denuding pipette 1 is filled with a liquid such as a mineral oil. The pressure sensing element of the pressure sensor 10 is connected to the control module 4 by a flexible electric wire. The control box 11 is physically separated from the manipulating handle 2 to form a separated type electric oocyte denuding device. A foot-operated switch controller 12 physically separated from the elements described above may be further provided, and in this case, the start-stop key 21, the accelerator key 22 and the decelerator key 23 on the panel of the manipulating handle 2 can be kept or removed.

In a fifth way, the oocyte denuding pipette 1 and the connecting port of the manipulating handle 2 are in a tight detachable connection, the bulb 8 and the pressure sensor 10 are mounted in the manipulating handle 2, and the drive module 3, the control module 4, the display module 5, the power module 6, the memory 7 and the voice module 9 are mounted in the control box 11. Part of the keys of the key module of the control module 4, such as keys for controlling starting, stopping, acceleration and deceleration, are connected to the start-stop key, the accelerator key and the decelerator key of the manipulating handle 2 by flexible electric wires. The micro-cylinder 311 in the drive module 3 is in communication with the oocyte denuding pipette 1 by a flexible pipeline, and the communicating pipeline between the micro-pushrod 312 and the oocyte denuding pipette 1 is filled with a liquid such as a mineral oil. The pressure sensing element of the pressure sensor 10 is connected to the control module 4 by a flexible electric wire. The control box 11 is physically separated from the manipulating handle 2 to form a separated type electric oocyte denuding device. A foot-operated switch controller 12 physically separated from the elements described above may be further provided, and in this case, the start-stop key 21, the accelerator key 22 and the decelerator key 23 on the panel of the manipulating handle 2 can be kept or removed.

An oocyte denuding method using the electric oocyte denuding device according to the present application is described as follows. In the case that oocyte denudation is performed before ICSI or before oocyte cryopreservation, an oocyte-corona-cumulus complex is transferred into a solution containing 80 IU/L hyaluronidase by a Pasteur pipette which is not drawn, and the oocyte-corona-cumulus complex is continuously blown and struck for several times to remove most of mucus clots, and then the predigested oocyte-corona-cumulus complex is transferred into an operational culture medium, the predigested oocyte-corona-cumulus complex is driven to repeatedly enter and exit from an orifice of the oocyte denuding pipette by a power for blowing and suctioning provided by the stepper motor 34 until the granular cell removal degree meets operational requirements.

The oocyte denuding method using the electric oocyte denuding device according to the present application may also be realized as follows. In the case that oocyte denudation is performed after IVF using test tube method, a suspension liquid of culture medium of the oocyte-corona-cumulus complex obtained after the IVF using test tube method is transferred to an empty culture dish by a Pasteur pipette which is not drawn, the oocyte-corona-cumulus complex is driven to repeatedly enter and exit from the orifice of the oocyte denuding pipette by a power for blowing and suctioning provided by the stepper motor until the granular cell removal degree meets operational requirements. In the case that oocyte denudation is performed after the IVF using micro drop method, an oocyte adhered to the bottom of the culture dish along with granular cells is repeatedly blown and sucked by a power for blowing and suctioning provided by the stepper motor 34, to be separated from the bottom of the culture dish, and then the oocyte is repeatedly blown and sucked till the granular cell removal degree meets the operational requirements.

The stepper motor 34 is controlled by the single-chip microcomputer 42. A program is set in the single-chip microcomputer 42, parameters of the program mainly include a blowing/suctioning frequency and a liquid column length. The liquid column length is adjusted by the stroke of the stepper motor 34. In the case that a liquid column length is certain, the blowing/suctioning frequency is adjusted by reciprocating frequency of the stepper motor 34, and correspondingly, the blowing/suctioning velocity and the corresponding blowing force and suctioning force are adjusted. The higher the blowing/suctioning frequency, the higher the blowing/suctioning velocity, and the greater the blowing force and suctioning force. The program for the single-chip microcomputer can be modified and/or stored into a new program at any time and can be started and stopped at any time.

The stepper motor 34 includes at least three velocity adjustment modes: alternately using pre-stored programs to adjust the velocity; manually increasing or decreasing a frequency value on the basis of the blowing/suctioning frequency of a running program, wherein the magnitude of increasing or decreasing the frequency value in a single operation can be set by programming; and automatically increasing the blowing/suctioning frequency to a certain set high value on the basis of the blowing/suctioning frequency by a running program, and maintaining at the set high value for a set duration, and then restoring to the original blowing/suctioning frequency.

The data of the oocyte denuding operation are recorded in the memory and can be viewed and/or outputted. The data of the oocyte denuding operation mainly include basic parameters of a running program such as a program numbering, a blowing/suctioning frequency and a length of liquid column; and program running data such as a real-time blowing/suctioning frequency, a start time and an end time of a certain blowing/suctioning frequency, an accumulated operation time at a certain blowing/suctioning frequency, a total operation time and other data.

The above embodiments are only preferable embodiments of the present application and are not intended to limit the present application. Any modifications, equivalent substitutions and improvements made within the spirit and principle of the present application should be deemed to fall into the scope of the present application.

The invention claimed is:

1. An electric oocyte denuding device, comprising:
an oocyte denuding pipette;
a manipulating handle; and
a drive module, a control module, a power module, a memory and a bulb which are mounted in the manipulating handle,
wherein one end of the manipulating handle is provided with a connecting port, the oocyte denuding pipette is connected to the connecting port; the drive module comprises a micro-cylinder module, a transmission mechanism and a stepper motor; the control module comprises a stepper motor driver, a single-chip microcomputer and a key module; the stepper motor driver, the key module, a display module, the power module and the memory are respectively connected to the single-chip microcomputer; the stepper motor driver is connected to the stepper motor; the stepper motor is connected to the transmission mechanism, and the transmission mechanism is connected to a micro-pushrod; another end of the micro-pushrod is arranged in a micro-cylinder, the micro-cylinder is in communication with a sealing tube of the oocyte denuding pipette; and the bulb is in communication with the oocyte denuding pipette.

2. The electric oocyte denuding device according to claim 1, wherein the oocyte denuding pipette is an oocyte denuding pipette tip, an oocyte denuding needle or an oocyte denuding Pasteur pipette.

3. The electric oocyte denuding device according to claim 1, wherein a start-stop key, an accelerator key and a decelerator key are provided on the manipulating handle, and are electrically connected to the key module respectively.

4. The electric oocyte denuding device according to claim 3, wherein a drive module bin and a main bin are provided in the manipulating handle; the drive module is received in the drive module bin; the control module and the power module are received in the main bin; and a display screen is further embedded in the manipulating handle.

5. The electric oocyte denuding device according to claim 3, wherein a central hole is provided at a center of the connecting port, a tail end of the central hole is narrowed to form a stop ring; the central hole is configured to receive the sealing tube, and the sealing tube is limited inside the central hole by the stop ring, and an outer wall of the sealing tube fits closely against an inner wall of the central hole; an opening at one end of the sealing tube is provided with a coupling configured to be in a tight plug-in connection with the oocyte denuding pipette; and an opening at another end of the sealing tube is provided with a coupling configured to be in a tight connection with a hose in communication with the micro-cylinder, a coupling configured to be in a tight connection with a hose in communication with the bulb, and a coupling configured to be in a tight connection with a hose connected to the pressure sensor.

6. The electric oocyte denuding device according to claim 1, wherein the micro-cylinder module comprises the micro-cylinder, the sealing tube, a pressing member and a pressing nut, wherein the micro-pushrod is connected to the micro-cylinder; the sealing tube is received in the micro-cylinder, the pressing member fits closely against the sealing tube, the pressing nut is connected to the micro-cylinder by screw threads, the pressing member has a part located inside the pressing nut and another part protruding from a circular opening of the pressing nut.

7. The electric oocyte denuding device according to claim 1, wherein the transmission mechanism comprises a screw rod and a nut-slider, the screw rod is connected to the stepper motor, and one end of the micro-pushrod is fixed to the nut-slider.

8. The electric oocyte denuding device according to claim 1, wherein the transmission mechanism comprises a spur gear and a spur rack-slider, the spur gear is assembled on the stepper motor, and one end of the micro-pushrod is fixed to the spur rack-slider.

9. The electric oocyte denuding device according to claim 1, further comprising a voice module, which is connected to the single-chip microcomputer.

10. The electric oocyte denuding device according to claim 1, further comprising a control box, which is connected to the manipulating handle by a cable.

11. The electric oocyte denuding device according to claim 10, wherein a display screen is provided on the control box; or, each of the manipulating handle and the control box is provided with a display screen.

12. The electric oocyte denuding device according to claim 1, further comprising a pressure sensor, wherein the pressure sensor is also connected to the single-chip microcomputer, and a pressure sensing element of the pressure sensor is in communication with the oocyte denuding pipette by a pipeline.

13. An oocyte denuding method using an electric oocyte denuding device, wherein, the electric oocyte denuding device comprises:
an oocyte denuding pipette;
a manipulating handle; and
a drive module, a control module, a power module, a memory and a bulb which are mounted in the manipulating handle,
wherein one end of the manipulating handle is provided with a connecting port, the oocyte denuding pipette is connected to the connecting port; the drive module comprises a micro-cylinder module, a transmission mechanism and a stepper motor; the control module comprises a stepper motor driver, a single-chip microcomputer and a key module; the stepper motor driver, the key module, a display module, the power module and the memory are respectively connected to the single-chip microcomputer; the stepper motor driver is connected to the stepper motor; the stepper motor is connected to the transmission mechanism, and the transmission mechanism is connected to a micro-pushrod; another end of the micro-pushrod is arranged in a micro-cylinder, the micro-cylinder is in communication with a sealing tube of the oocyte denuding pipette; and the bulb is in communication with the oocyte denuding pipette; and
wherein, the oocyte denuding method comprises the following steps: transferring an oocyte-corona-cumulus complex into a solution of hyaluronidase by a Pasteur pipette which is not drawn, continuously blowing and striking the oocyte-corona-cumulus complex for a plurality of times to remove most of mucus clots, and then transferring the oocyte-corona-cumulus complex which is predigested into an operational culture medium, driving the oocyte-corona-cumulus complex which is predigested to repeatedly enter and exit from an orifice of the oocyte denuding pipette by a power for blowing and suctioning provided by the stepper motor until a granular cell removal degree meets an operational requirement.

14. The oocyte denuding method according to claim 13, wherein the stepper motor is controlled by the single-chip microcomputer and comprises at least three velocity adjustment modes: alternately using pre-stored programs to adjust a velocity; manually increasing or decreasing a frequency value on the basis of a blowing/suctioning frequency of a running program, wherein a magnitude of increasing or decreasing the frequency value in a single operation is settable by programming; and automatically increasing a blowing/suctioning frequency to a certain set high value on the basis of the blowing/suctioning frequency of the running program, and maintaining at the set high value for a set duration, and then restoring to an original blowing/suctioning frequency.

15. An oocyte denuding method using an electric oocyte denuding device, wherein, the electric oocyte denuding device comprises:
an oocyte denuding pipette;
a manipulating handle; and
a drive module, a control module, a power module, a memory and a bulb which are mounted in the manipulating handle,
wherein one end of the manipulating handle is provided with a connecting port, the oocyte denuding pipette is connected to the connecting port; the drive module comprises a micro-cylinder module, a transmission mechanism and a stepper motor; the control module comprises a stepper motor driver, a single-chip microcomputer and a key module; the stepper motor driver, the key module, a display module, the power module and the memory are respectively connected to the single-chip microcomputer; the stepper motor driver is connected to the stepper motor; the stepper motor is connected to the transmission mechanism, and the transmission mechanism is connected to a micro-pushrod; another end of the micro-pushrod is arranged in a micro-cylinder, the micro-cylinder is in communication with a sealing tube of the oocyte denuding pipette; and the bulb is in communication with the oocyte denuding pipette; and
wherein, the oocyte denuding method comprises the following steps: in a case that oocyte denudation is performed after IVF using test tube method, transferring a suspension liquid of cultural medium of an oocyte-corona-cumulus complex to an empty culture dish by a Pasteur pipette which is not drawn, driving the oocyte-corona-cumulus complex to repeatedly enter and exit from an orifice of the oocyte denuding pipette by a power for blowing and suctioning provided by the stepper motor until a granular cell removal degree meets an operational requirement; and in a case that oocyte denudation is performed after IVF using micro drop method, repeatedly blowing and suctioning an oocyte adhered to a bottom of a culture dish along with granular cells by a power for blowing and suctioning provided by the stepper motor, to separate the oocyte from the bottom of the culture dish, and then repeatedly blowing and suctioning the oocyte until a granular cell removal degree meets an operational requirement.

16. The oocyte denuding method according to claim 15, wherein the stepper motor is controlled by the single-chip microcomputer and comprises at least three velocity adjustment modes: alternately using pre-stored programs to adjust a velocity; manually increasing or decreasing a frequency value on the basis of a blowing/suctioning frequency of a running program, wherein a magnitude of increasing or decreasing the frequency value in a single operation is settable by programming; and automatically increasing a blowing/suctioning frequency to a certain set high value on the basis of the blowing/suctioning frequency of the running program, and maintaining at the set high value for a set duration, and then restoring to an original blowing/suctioning frequency.

* * * * *